United States Patent [19]

Petzold

[11] Patent Number: 5,350,500
[45] Date of Patent: Sep. 27, 1994

[54] ELECTROKINETIC POTENTIAL MEASUREMENT

[75] Inventor: James C. Petzold, Reading, Great Britain

[73] Assignee: The Wiggins Teape Group Limited, Basingstoke, United Kingdom

[21] Appl. No.: 39,058

[22] PCT Filed: Oct. 4, 1991

[86] PCT No.: PCT/GB91/01731
§ 371 Date: Apr. 5, 1993
§ 102(e) Date: Apr. 5, 1993

[87] PCT Pub. No.: WO92/06368
PCT Pub. Date: Apr. 16, 1992

[30] Foreign Application Priority Data

Oct. 8, 1990 [GB] United Kingdom ............... 9021830.6

[51] Int. Cl.⁵ ............................................. G01N 27/26
[52] U.S. Cl. ..................................... 204/409; 204/412; 204/415; 204/130; 204/132; 204/252; 324/71.1; 324/425; 324/450
[58] Field of Search ............... 204/406, 407, 408, 412, 204/415, 252, 130, 132; 324/71.1, 425, 450

[56] References Cited

U.S. PATENT DOCUMENTS 4,535,285   8/1985   Evans et al. ..................... 324/71.1

Primary Examiner—John Niebling
Assistant Examiner—Bruce F. Bell
Attorney, Agent, or Firm—Burns, Doane, Swecker & Mathis

[57] ABSTRACT

The measurement of electrokinetic potential is of importance in paper-making. A measuring cell (12) for a specific potential known as streaming potential of the kind disclosed in EP B1 0 079 726 is now provided with measuring electrodes (40, 42) of a metal which forms a reversible electrochemical reaction with pure water to oxidize the metal. The electrodes (40, 42) used in the measurement mode in the cell have a film comprising an oxide of the metal electrochemically formed thereover. Such electrodes are found to give more stable and consistent measurement than the stainless steel electrodes used previously. Silver, lead, copper and alloys such as lead and silver are preferred. The measuring electrodes (40, 42) are regenerated within the cell (12) through electrochemical reduction to bare metal, followed by oxidation to re-form the film. This is performed with the aid of auxiliary electrodes (60, 62) in the cell. A control system (50) for the measurement and regeneration mode is described. Excess excursions of the measurement mode voltage are monitored to indicate that the regeneration procedure is to be entered. The measuring electrode (42) in the cell compartment (22) in which the measurement pad is formed is provided with a shroud (13) to protect it during the flushing of the pad from the mesh (14) in the cell.

19 Claims, 3 Drawing Sheets

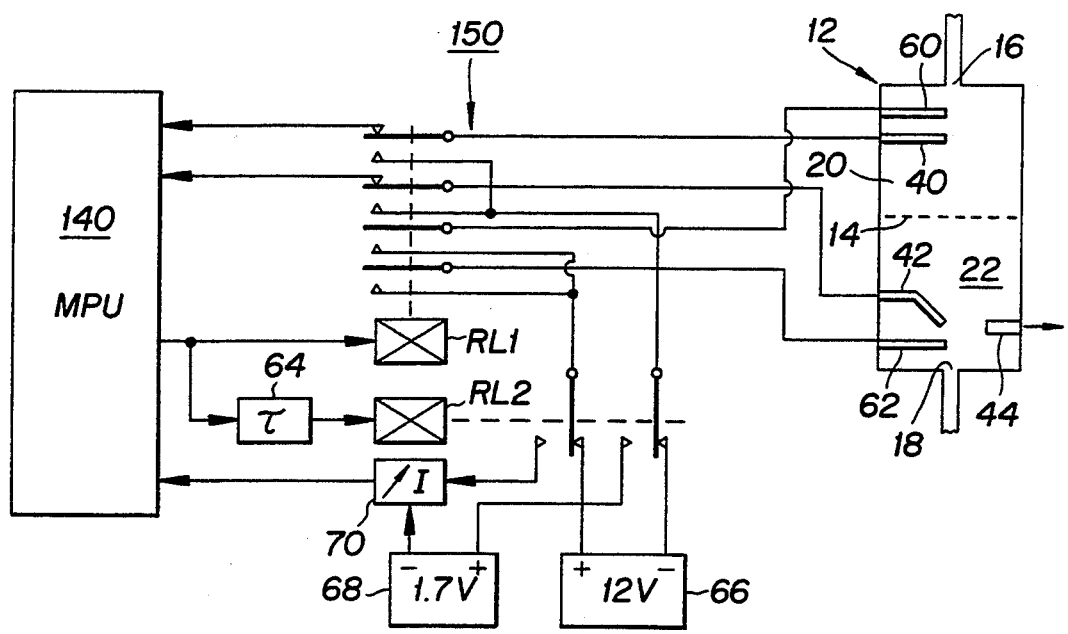
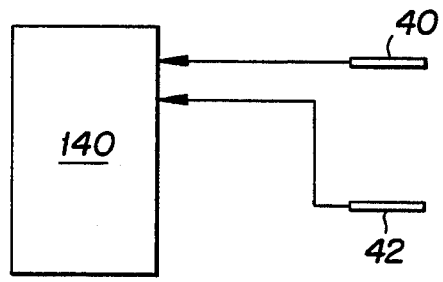
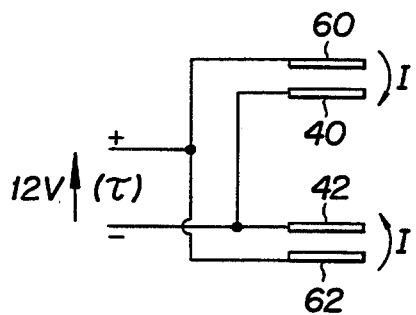
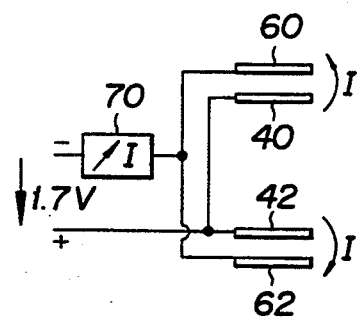

ELECTROKINETIC POTENTIAL MEASUREMENT

FIELD OF THE INVENTION

This invention relates to a measuring cell of the kind used in the measurement of an electrokinetic potential, for example of a fibrous or granular dispersion, and to a measuring system incorporating such a cell. It also relates to a measurement system for the measurement of an electrokinetic potential incorporating such a cell, and to a method of maintaining the condition of a measurement electrode or a pair of electrodes in such a cell.

More particularly, electrical characteristics due to electrokinetic phenomena are of industrial interest. Electrokinetic potentials are of importance in so far as they occur in fibrous and granular dispersions, such as stock for making paper, mineral ores or flocculated sewage sludge. Paper stock is a dispersion of cellulose fibres, together with fillers and other additives, in water. In paper making a particular manifestation of an electrokinetic potential is Zeta potential which is conventionally measured by way of another potential called streaming potential. European Patent EP B1 0 079 726 (Wiggins Teape) describes the construction of a measuring cell for the measurement of streaming potential, and the arrangement of the complete cell system including flow circuitry and manner of operation with a view to obtaining consistent and reliable measurement from the feed stock or furnish as supplied to the wire of a paper-making machine.

BACKGROUND OF THE INVENTION

FIG. 1 of EP B1 079 726 shows the main elements of the described measuring cell. The cell cavity is divided into two compartments by a mesh. As illustrated the mesh is horizontal, providing upper and lower compartments. A respective measuring electrode projects into each compartment. The operation of the cell in brief is that the paper stock is fed to the lower compartment to build a pad of fibrous material on the underside of the mesh, the cell being generally full of the water component of the stock. The pad is then subject to controlled pressure conditions across the pad and a potential difference measurement is made between the electrodes at the established pressures to obtain a measurement of streaming potential. This is discussed in detail in the prior patent.

The described measurement cell and its manner of operation are considered to provide a substantial advance in the art of measuring streaming potential, particularly in providing an effective means of on-line measurement on a paper-making machine. The cell particularly described in the patent utilises stainless steel electrodes. It was found that in long-term use, irregularities and drifts could arise in measurements made with the cell. Investigation has revealed that these irregularities were related to an electrochemical potential effects arising from oxidation of the stainless steel. The nature of the surface oxide film that forms on stainless steel is very variable.

In seeking for alternative materials it has also been found that avoiding the build up of an oxide film is not necessarily the answer. The present investigation has shown that there may also be a capacitance effect at the electrode/water interface which causes drift in potential measurement. This capacitance is very high. Measurements on gold electrodes, which do not readily oxidize, have indicated a capacitance value of 20 $\mu F/cm^2$.

This capacitance is a direct consequence of polarization of the electrode in the stock being measured. There is an inevitable but quantifiable polarization in tap water. However, polarization effects also result from chemicals being absorbed onto the electrodes from the stock being measured. These are not quantifiable, particularly having regard to the wide variation that occurs in the constituents of paper-stock. It has been found that gold electrodes suffer from such absorption. The electrode then forms the equivalent of a polarized electrolytic capacitor with an ionised layer in the stock within a few molecules of the electrode surface. This gives rise to the high capacitance per unit area quoted above and the better the quality of the capacitor formed, that is the lower the leakage current, the less suited is the electrode for the measurements required.

Thus there is a general requirement to use for the electrodes metals that have the least possible polarization and for any resulting capacitance to be of poor quality, that is have a high leakage current. The metals proposed in accordance with the present invention have a reversible electrochemical reaction with pure water to oxidise the metal.

SUMMARY OF THE INVENTION

There will be described hereinafter a measuring cell which has silver/silver oxide electrodes that substantially meet the requirements discussed above. The cell to be described and circuitry associated with it also provides the means of obtaining the desired performance of the cell over prolonged use.

Broadly stated, according to a first aspect of the present invention there is provided a cell for the measurement of an electrokinetic potential comprising two compartments separated by a mesh on which a pad is to be formed and a respective measuring electrode in each compartment, characterised in that; each measuring electrode is of a metal which forms a reversible electrochemical reaction with pure water to oxidise the metal, each electrode has a film comprising an oxide of the metal electrochemically formed thereover, and the metal is selected from silver, lead, copper, iridium, bismuth and germanium, and alloys thereof.

According to a second aspect of the invention there is provided a cell for the measurement of an electrokinetic potential comprising two compartments separated by a mesh on which a pad is to be formed and a respective measuring electrode in each compartment, characterised in that each measuring electrode is of a metal selected from silver, lead, copper, iridium, bismuth and germanium, and alloys thereof.

In a preferred cell construction a shroud device is disposed between the mesh and the measuring electrode in that compartment in which the pad is formed in order to protect this electrode from damage by pad material upon flushing of the pad from the mesh. In the construction to be described, the shroud-protected electrode projects into the compartment in which the pad is formed from a side wall of the compartment. More particularly it projects in a direction inwardly and away from the mesh, that is downwardly in the normal orientation of the cell in use. The shroud device comprises a ring portion secured to the electrode at the side wall and a protective portion that extends parallel to and spaced from the inwardly projecting electrode. The shroud device is of an electrically inert material.

The cell of the invention preferably includes at least one auxiliary or counter electrode in the cell for use as a cathode with respect to said measuring electrodes acting as an anode for the electrochemical formation of an oxide film on said measuring electrodes in the presence of water in the cell. In practice the water will be mains supply water or whatever other water source is available. The cell construction to be described uses a pair of auxiliary electrodes, one in each compartment located outwardly with respect to the mesh of the measuring electrode in that compartment, i.e. the measuring electrode lies between the associated auxiliary electrode and the mesh.

The auxiliary electrode, or pair of electrodes, is not only usable in the oxidation of the measuring electrodes but in their reduction to the base metal when electrode regeneration is required.

In another aspect of the invention there is provided a measurement system for the measurement of an electrokinetic potential, comprising a cell embodying the invention as set forth above; and means connected to said measuring electrodes to obtain electrokinetic potential measurements from the cell, said means being operable to monitor excursions of said electrokinetic potential measurement beyond a predetermined limit indicative of the measuring electrodes being in need of re-forming of the metal oxide film thereon. It will be shown how the re-forming of a metal oxide film can be performed within the cell and without disassembly of the cell, with the aid of the one or more auxiliary electrodes, or possibly the mesh connected to act as an auxiliary electrode.

In yet another aspect of the invention there is provided a measurement system for measurement of an electrokinetic potential comprising a measurement cell embodying the invention and including at least one auxiliary electrode, the system further comprising
means for supplying first and second voltages;
means for receiving electrokinetic potentials from said cell measuring electrodes and operable to monitor excursions of the electrokinetic potential beyond a predetermined limit;
means interconnecting said voltage supply means, said potential monitoring means and said measuring and auxiliary electrodes and controlled by said potential monitoring means to operate in three modes:
a first mode in which said potential monitoring means is connected to said measurement electrodes to receive electrokinetic potentials therefrom;
a second mode initiated in response to an excursion of the electrokinetic potential beyond said predetermined limit and in which said measuring electrodes and said at least one auxiliary electrode are connected to the negative and positive poles respectively of said first voltage supply for effecting a reduction of said measuring electrodes to the metal; and
a third mode in which said measuring electrodes and said at least one auxiliary electrode are connected to the positive and negative poles respectively of said second voltage supply for effecting an oxidation of said measuring electrodes to form a fresh oxide film thereon.

The foregoing measurement system may further comprise a timer for establishing the duration of the second mode to be a predetermined time. The system may comprise current-sensing means responsive to the electrode current to at least one of the measuring electrodes during the third mode to determine when the current falls below a predetermined value indicative of the oxide film having been sufficiently formed. The third mode may then be terminated at this point and the cell restored to operating in the first mode. As is described more fully below, these procedures for monitoring the condition of the measuring electrodes and re-forming the oxide when necessary may be carried out without any need to remove or disassemble the cell. This is of particular advantage where the cell is employed in on-line measurement in a paper-making machine.

In a further aspect of the invention there is provided a method of maintaining the condition of a measuring electrode in a cell embodying the invention, whether or not it includes one or more auxiliary electrodes, which method comprises:

connecting the measuring electrode as the cathode in an electrolyte and passing current through the electrode to effect reduction thereof to the metal, and connecting the electrode as the anode in an electrolyte to effect oxidation thereof whereby a fresh oxide film is formed on the electrode.

Preferably the electrolyte during reduction is water. Water may be used as the electrolyte during both reduction and oxidation. As already indicated above, the preferred practice of the invention enables the electrode to be subject to reduction and oxidation in situ in the cell. Preferably both measuring electrodes are connected in parallel for simultaneous reduction and oxidation in situ in the cell. As already discussed at least one auxiliary or counter electrode is preferably located in the cell to provide an anode and cathode respectively for the reduction and oxidation actions.

In performing the reduction and oxidation actions it is preferred that the magnitude of voltage applied during reduction is substantially greater than that applied during oxidation. The reduction action is preferably effected for a predetermined time, in practice chosen to ensure that reduction is complete. The oxidation action may be effected until the current through the measuring electrode or electrodes, as the case may be, falls below a predetermined value. The practical selection of this current value at a level at which the oxide is re-formed on the electrode is discussed further below.

BRIEF DESCRIPTION OF THE FIGURES

The invention and its presently preferred practice will now be described with reference to the accompanying drawings in which:

FIG. 1 shows a cell embodying the invention connected in a measuring system in accord with the invention;

FIGS. 2, 3 and 4 show the cell electrode connections in the measurement mode, cleaning mode and re-oxidation mode respectively;

THE PREFERRED EMBODIMENTS

Figure 5A:
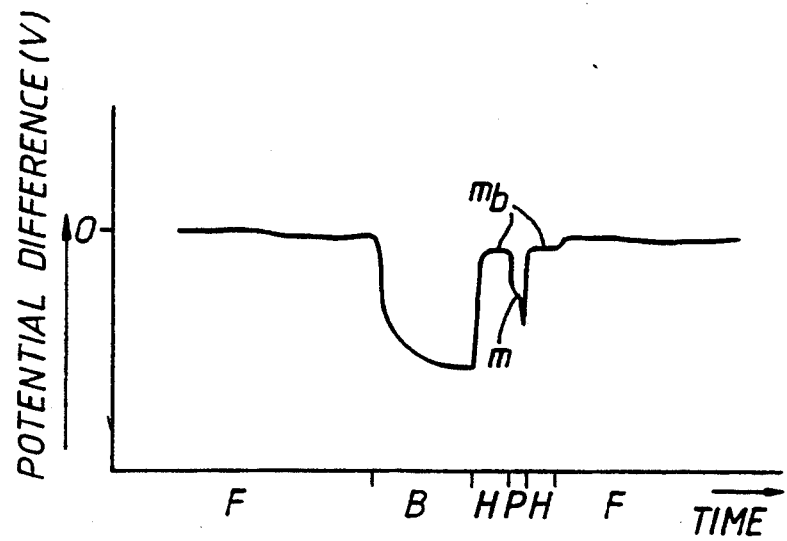
FIGS. 5A and 5B show measurement cycle responses: using $Ag/Ag_2O$ measuring electrodes in accord with the invention and gold electrodes respectively.

The figure shows a cell 12 in a generally vertical orientation having a horizontal mesh 14 across the cell dividing the cell into upper and lower compartments 20 and 22 having respective upper and lower ports 16 and 18.

Within the cell are located electrodes 40 and 42 in the respective upper and lower compartments 20 and 22. The cell may also contain a pressure transducer 44 mounted to sense pressure applied in the lower compartment 22. The measuring cell 12 thus far described is connected in a flow circuit as shown in FIG. 1 of abovementioned specification EP B1 0 079 726 to be used for measurement in the manner described in the prior patent. This includes obtaining potential difference measurements between the electrodes 40 and 42 which are processed in microprocessor 140 to obtain streaming potential measurements. It is to be noted that the horizontal orientation of the mesh 14 is preferred for the reasons discussed in the prior patent but this is not an essential feature of the present invention.

The present measuring cell also includes a pair of auxiliary electrodes 60 and 62 mounted in the upper and lower compartments 20 and 22 respectively and additional circuitry 150 controlled by the microprocessor 140. The electrodes 40 and 42 are of silver, conveniently of silver wire of say 2 mm. diameter. The electrodes 60 and 62 act as counter electrodes in the regeneration of the measuring electrodes as will be described, and may be of any conductive material such as stainless steel. It is to be noted that the counter electrodes are preferably mounted exterior to the measurement path between the measurement electrodes 40, 42 so as to have as little effect as possible on the measurement conditions within the cell. The circuitry is such that the counter electrodes are electrically isolated from one another during the measurement mode so that no circulating path exists between them. The present measurement system performs the following main functions with the additional circuitry just-described.

1) In a normal measurement mode (FIG. 2) excessive excursions of the difference voltage between electrodes 40 and 42 are monitored by the microprocessor to initiate a cleaning/re-forming procedure for the electrodes;
2) on sensing excessive excursions of the difference voltage, the microprocessor initiates an electrode cleaning mode (FIG. 3) with the aid of the counter electrodes 60, 62 to reduce the electrodes 40 and 42 to the bare silver; and
3) the microprocessor then initiates a re-oxidation mode (FIG. 4) for electrodes 40 and 42 to re-form the oxide film, this process also being performed with the aid of counter electrodes 60, 62. This step is carried out while flushing the cell with water.

In FIG. 1 the circuit 150 is shown in terms of relay control to achieve the three modes above-listed. However, it will be appreciated that many forms of circuit, including fully electronic, can be designed to achieve the same functions.

FIG. 1 shows the circuitry in the normal operating mode in which neither of the relays RL1 and RL2 is energised. The relay contacts are shown in this non-energised state. The electrodes 40 and 42 are connected to the microprocessor 140 for measurement of the potential difference between them as described in the patent EP B1 0 079 726. The electrodes 60,62 are electrically isolated from one other by open contacts of relay RL1 and they are disconnected from the remaining circuitry in the measurement mode so as to be of no effect. In particular, no circulating path can be established between electrodes 60 and 62. The result is the measuring mode circuit of FIG. 2 equivalent to FIG. 1 of the prior patent.

In practice in the application of the cell to measuring paper feed stock, the difference potential is expected to be of the order of none to several millivolts, say 0–10 mV (plus or minus) for the measurement conditions applied. In addition to its measurement function, the microprocessor is programmed to look for potential excursions beyond the range of values to be expected. This is a somewhat arbitrary value selected in dependence upon what fibrous dispersion is being measured and the precise conditions of measurement. For example in the present example the pressure applied directly affects the potential measured. However, in the present case it can be expected that an excursion of voltage beyond say ±20 mV is indicative that the cell is not functioning as is desired and that the electrode cleaning mode should be initiated. It would, of course, be possible to adopt a more arbitrary criterion for entering the electrode cleaning mode based on time or a selected number of cell cycles.

The cleaning mode is entered by the microprocessor activating relay RL1 (via an appropriate relay driver if required) and a timer 64 through which relay RL2 is activated. Thus at this stage RL2 remains unenergised with its contacts as in the position shown in FIG. 1. The resultant circuit is shown in FIG. 3. The measurement electrodes are connected together to the negative pole of a power supply unit 66, the counter electrodes are now connected together to the positive pole. By making the measurement electrodes the cathode, the oxide is reduced. The ideal is to restore the electrode to clean silver which could be monitored visually. In practice it is simpler to continue the cathodic reduction for a sufficient period of time ($\tau$) to ensure the restoration of the electrode to have a silver surface. This is done by means of timer 64. In the cell on which experiments have been performed the measurement electrodes are about 1.5 cms long and 2 mm diameter and a timer interval ($\tau$) of about 2 mins has been found sufficient. The reduction action produces gassing of hydrogen from the measurement electrodes which aids in loosening and detaching contaminants from the electrodes.

When the timer period ($\tau$) elapses, the timer 64 energises relay RL2 to change-over the power supply to unit 68. The measurement electrodes remain connected together as do the counter electrodes. However, the polarity of the voltage supplied is reversed and is lower. A voltage of 1.7 V has been found to provide a good adherent oxide film on the electrode. This lower voltage is applied for say 30 minutes. The measurement electrodes 40, 42 are now the anodes within the cell. This oxidation stage is shown in FIG. 4.

The cell electrolyte in both the cleaning and oxide forming phases is simply the ordinary mains water supply which is used to flush the cell and with which the cell will ordinarily be filled whilst the system is inactive between measurements.

Various oxidation reactions are possible in tap water to produce the oxides of silver, silver carbonate or silver chloride. The colour of the oxide film has been found to be brown/black suggesting that what is formed is an oxide and the oxide is predominantly $Ag_2O$. The three possibilities involving oxides are:

| Equation | Oxide Colour | Electrode potential (V) |
|---|---|---|
| 1) $Ag_2O + H_2O + 2e^- \rightleftharpoons 2Ag + 2OH^-$ | $Ag_2O$: brown/black | 0.342 |
| 2) $Ag_2O_3 + H_2O + 2e^- \rightleftharpoons 2AgO + 2OH^-$ | $Ag_2O_3$: ? | 0.740 |
| 3) $2AgO + H_2O + 2e^- \rightleftharpoons Ag_2O + 2OH^-$ | AgO: grey/black | 0.599 |

Electrode potential measurements have indicated that Equation 1) predominates. It will be noted that the electrode potential is dependent on the pH. Provided that the pH values in the upper and lower compartments of the cell are the same in operation, the back-to-back potential difference between the electrodes should be zero and thus not affect the actual streaming potential measurements. In practice it has been found that this quiescent electrode potential difference is very close to zero.

It will, of course, be appreciated that by using ordinary mains or tap water, the electrode potentials may be affected to some extent by other chemicals in the tap water, for example chloride.

When the oxidation phase of FIG. 4 commences, current I flows easily. In theory it is easy to arrive at the total electric charge required to provide an oxide film over the electrodes and to measure the total charge delivered. A more practical route arises from the fact that as the oxide film forms the current drops according to an exponential law until what may be called a leakage current is reached. It is convenient, therefore, to monitor the current and terminate the oxidation phase upon a preselected lower current value being achieved. To this end a current monitoring device 70 is connected in the current path to provide an output signal which the current drops to a value of say 5 $\mu A$. This signal is sent to the microprocessor which terminates the activation of both relay RL1 and R12 and restores the circuit to the condition of FIGS. 1 and 2 for further streaming potential measurement.

Figure 5B:
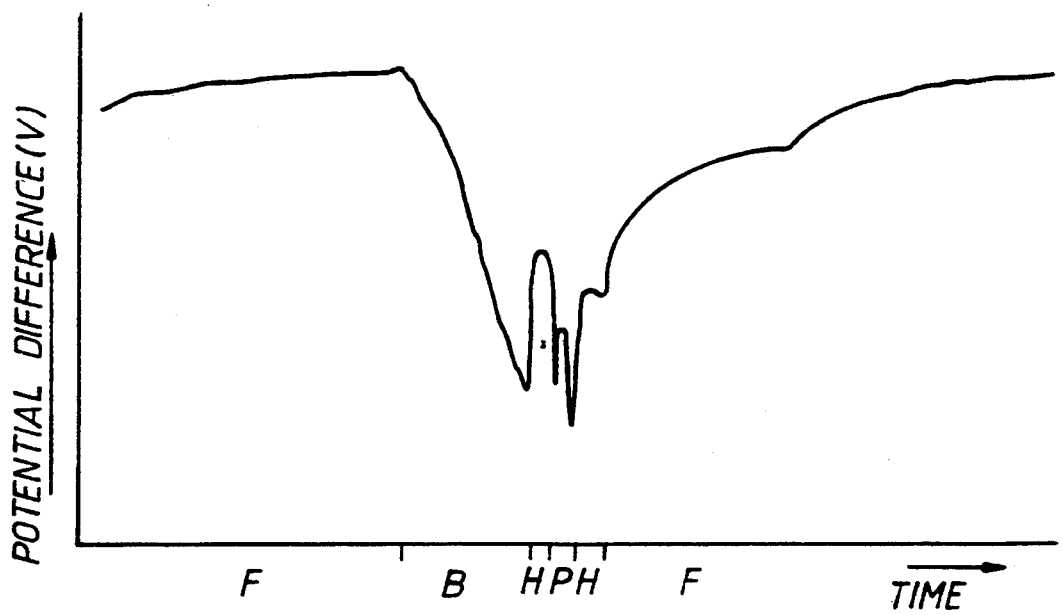

An example of a streaming potential measurement sequence is shown in FIGS. 5A and B which show a comparison between measurements made with the Ag-/$Ag_2O$ electrodes (FIG. 5A) in which the oxide film is formed as described and gold electrodes (FIG. 5B). In each case after a previous cell flushing operation F there is a pad building operation B followed by a pad hold phase H at which a reference streaming potential measurement $m_b$ is made at or near zero pressure, a pad pulse phase P at which a streaming potential measurement m is made at a predetermined pressure (avoiding the transient spike), a second pad hold phase H at low pressure for another reference measurement $m_b$, and finally a flushing F of the pad from the cell. This sequence is substantially in accord with that described in EP B1 0 079 726 with reference to FIG. 4. It will be noted that in FIG. 5A the various signals levels are well defined. The two hold phases are equal. This is indicative of the Ag/$Ag_2O$ electrodes having little polarization or capacitance. What is also important is that this measurement sequence may be repeated many times with highly consistent results before the electrode performance deteriorates and cleaning and re-forming of the oxide film is required.

In comparison FIG. 5B shows a similar sequence of measurements made with gold measurement electrodes. The ill-defined response exhibits substantial polarization and capacitance effects.

The cell and the system described have been disclosed in terms of an automatic operation in situ in the cell. It is clearly preferably to avoid extracting the measurement electrodes from the cell though their cleaning and re-oxidation could be done externally. If they are to be cleaned and restored in the cell, then it is convenient though not essential to have the counter or counter electrodes a permanent part of the cell fittings. It is contemplated that if the mesh is of metal, e.g. stainless steel, it could provide a common counter-electrode for both measurement electrodes. All that need then be done is to make provision for external electrical connection to the mesh.

The circuitry shown is merely illustrative. It and the necessary voltage supplies can be arranged in many ways. Devices such as timers may well be realizable as part of the microprocessor itself.

Although the foregoing has particularly described the use of silver/silver oxide—specifically Ag/$Ag_2O$—as the electrode system, other metals which form a reversible electrochemical reaction with pure water to oxidise the metal are contemplated. Lead or a silver-/lead alloy or copper is considered suitable. Other metals having the appropriate electrochemical properties are Iridium, Bismuth, Barium and Germanium. There are other factors, of course, which may make various of the metals unsuitable in practice used on their own. Barium gives rise to potential toxicity problems. In a cell used on-line in a paper machine, barium may result in an unacceptable discharge of toxic effluent. Alloys of the above metals are also contemplated.

In the silver/silver oxide example described above the reversibility of the relevant electrochemical reaction—predominantly equation 1)—is of importance in the measurement mode. It allows the measurement electrodes to achieve an equilibrium in the stock being measured which maintains a potential balance between the electrodes. Without such equilibrium, potentials could arise to interfere with the wanted measurement potential. This reversibility of reaction is thus desirable in any electrode material.

Figure 6:
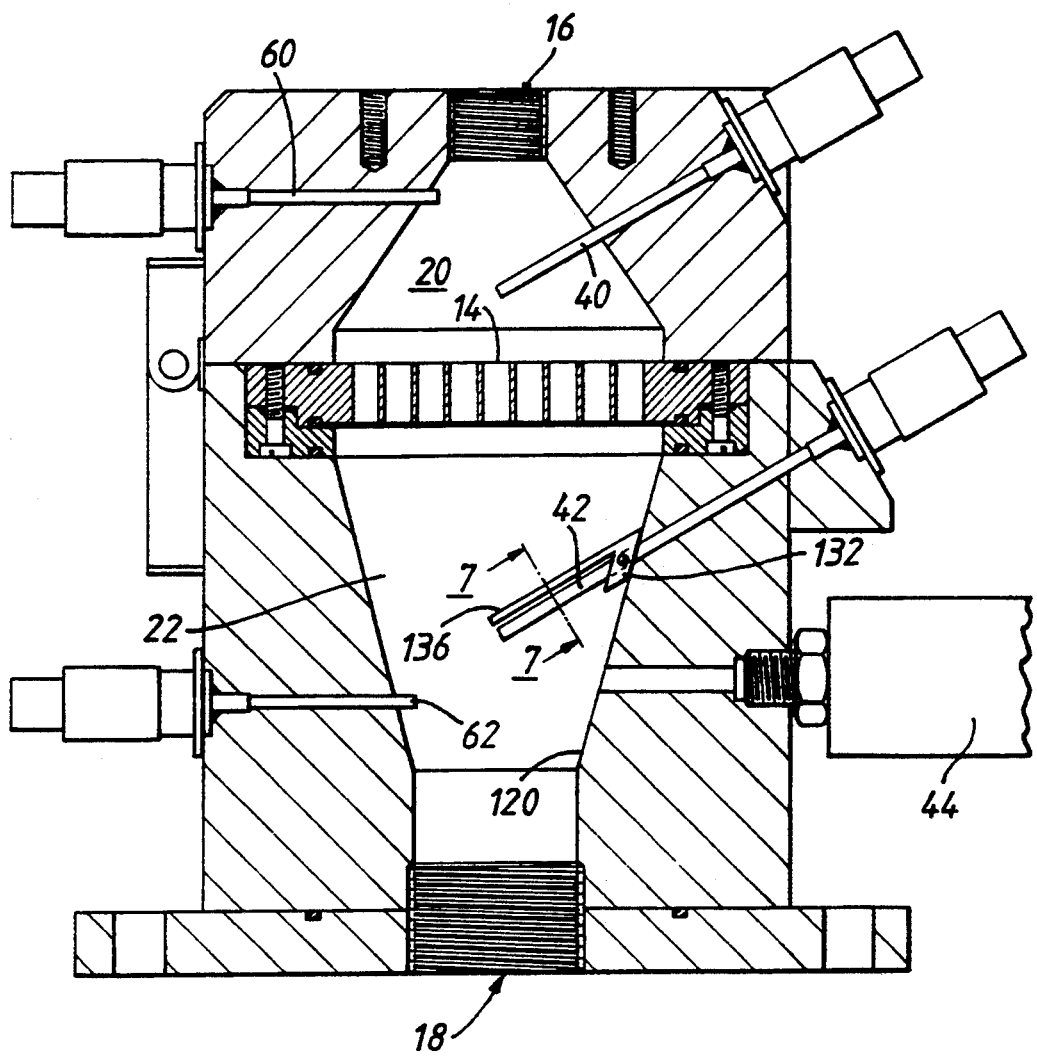
FIG. 6 shows a measuring cell similar to that shown in EP-B 0079726 but also incorporating counter electrodes and a protective shroud for the measuring electrode in the lower cell compartment.
Figure 7:
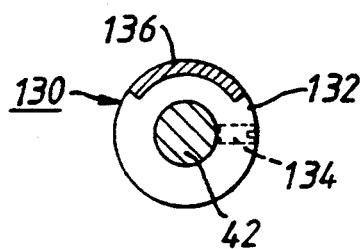
FIG. 7 shows an enlarged section of the shroud on 7—7 in FIG. 6.

In the practical employment of these electrodes, abrading of the oxide coating on the electrodes also needs to be taken into account. This is particularly relevant as regards the measurement electrode on the pad side of the cell mesh. That is the electrode 42 in the lower cell compartment 22. It has to sustain the contact of the material of the relatively hard pad being flushed out of the cell at the completion of a measurement cycle. The oxide may be protected from damage by using a shroud as seen in FIGS. 6 and 7. The silver wire electrode 42 is shown as a straight element projecting from the cell wall 120 downwardly into the cell chamber 22 below the mesh 14 and is protected by a rigid shroud device 130 above the electrode that comprises a ring portion 132 abutting wall 120 and secured on the wire 42 by a grub screw 134; and a convex shroud 136 above and spaced from the wire 42 by say 2 mm to act as a protective roof to prevent erosion of the electrode by the solids content of the stock during the back flushing sequence in which the pad is removed. The shroud device is made of an electrically inert plastic such as polytetrafluoroethylene (PTFE).

The shroud also provides a mechanical protection to the silver electrode, though in practice a 2 mm. diameter electrode shows sufficient rigidity. The electrodes 40 and 42 could also be provided by silver plating a harder base metal. The protection against oxide abrasion provided by the shroud device 130 applies generally to the electrode 42 whatever the metal of which it is made.

FIG. 6 also serves to show how the counter electrodes 60, 62 and measuring electrodes 40, 42 may be located in a practical cell structure having inlet and outlet ports 16 and 18 respectively and a mesh 14.

I claim:

1. A cell for the measurement of an electrokinetic potential comprising two compartments separated by a mesh on which a pad is to be formed and a respective measuring electrode in each compartment, characterised in that: each measuring electrode is of a metal which forms a reversible electrochemical reaction with pure water to oxidise the metal, each electrode has a film comprising an oxide of the metal electrochemically formed thereover, and the metal is selected from the group consisting of silver, lead, copper, iridium, bismuth, germanium, and alloys thereof.

2. A cell for the measurement of an electrokinetic potential comprising two compartments separated by a mesh on which a pad is to be formed and a respective measuring electrode in each compartment, characterised in that each measuring electrode is of a metal selected from the group consisting of silver, lead, copper, iridium, bismuth, germanium, and alloys thereof.

3. A cell as claimed in claim 1 or 2 in which a shroud device is disposed between the mesh and the measuring electrode in that compartment in which the pad is formed in order to protect this electrode from damage by pad material upon flushing of the pad from the mesh.

4. A cell as claimed in claim 3 in which the shroud-protected electrode projects in to the compartment, in which the pad is formed, from a side wall of the compartment, and the shroud device comprises a ring portion secured to the electrode at the side wall and a protective portion that extends parallel to and spaced from the inwardly projecting electrode, said shroud device being of an electrically inert material.

5. A cell as claimed in any one of claims 1 or 2 further comprising at least one auxiliary electrode in the cell for use as a cathode with respect to said measuring electrodes acting as a anode for the electrochemical formation of an oxide film on said measuring electrodes in the presence of water in said cell.

6. A measurement system for measurement of an electrokinetic potential comprising:
a measuring cell as claimed in claim 5;
means for supplying first and second voltages;
means for receiving electrokinetic potentials from said cell measuring electrodes and for monitoring excursions of the electrokinetic potential beyond a set limit;
means interconnecting said voltage supply means, said potential monitoring means and said measuring and auxiliary electrodes and controlled by said potential monitoring means to sequentially operate in each of three modes:
a first mode in which said potential monitoring means is connected to said measuring electrodes to receive electrokinetic potentials therefrom;
a second mode initiated in response to an excursion of the electrokinetic potential beyond said predetermined limit and in which said measuring electrodes and said at least one auxiliary electrode are connected to the negative and positive poles respectively of said first voltage supply for effecting a reduction of said measuring electrodes to the metal; and
a third mode in which said measuring electrodes and said at least one auxiliary electrode are connected to the positive and negative poles respectively of said second voltage supply for effecting an oxidation of said measuring electrodes to form a fresh oxide film thereon.

7. A cell as claimed in claim 5 in which a respective auxiliary electrode is provided in each cell compartment and is located with respect to the mesh outwardly of the measuring electrode in that compartment.

8. A measurement system as claimed in claim 7 further comprising a timer for establishing the duration of said second mode to be a set time.

9. A measurement system for the measurement of an electrokinetic potential comprising:
a cell as claimed in any one of claims 1 or 2; and
means connected to said measuring electrodes to obtain electrokinetic potential measurements from the cell, said means for monitoring excursions of said electrokinetic potential measurement beyond a set limit indicative of the measuring electrodes needing re-forming of a metal oxide film thereon.

10. A measurement system as claimed in claim 9 further comprising current-sensing means responsive to the electrode current to at least one of said measuring electrodes during said third mode to determine when the current falls below a set value indicative of the oxide film having been formed.

11. A method of maintaining the condition of a measuring electrode in a cell as claimed in any one of claims 1 or 2, which method comprises:
connecting the measuring electrode as the cathode in an electrolyte and passing current through the electrode to effect reduction thereof to the metal, and subsequently connecting the electrode as the anode in an electrolyte to effect oxidation thereof whereby a fresh oxide film is formed on the electrode.

12. A method as claimed in claim 11 in which the electrolyte during reduction is water.

13. A method as claimed in claim 11 in which the electrolyte during reduction and oxidation is water.

14. A method as claimed in claim 11 in which the electrode is subject to the reduction and oxidation actions in situ in the cell.

15. A method as claimed in claim 14 in which both measuring electrodes are connected in parallel for simultaneous reduction and oxidation in situ in the cell.

16. A method as claimed in claim 15 in which at least one auxiliary electrode is located in the cell to provide an anode and cathode respectively for the reduction and oxidation actions.

17. A method as claimed in claim 11 in which the magnitude of voltage applied during the reduction action is greater than that applied during the oxidation action.

18. A method as claimed in claim 11 in which the reduction action is effected for a set time.

19. A method as claimed in claim 11 in which the oxidation action is effected until the current flowing through the measuring electrode or electrodes, as the case may be, falls below a set value.

* * * * *